(12) United States Patent
Stuart

(10) Patent No.: US 7,267,944 B1
(45) Date of Patent: Sep. 11, 2007

(54) METHODS AND COMPOSITIONS FOR COMBINATORIAL-BASED DISCOVERY OF NEW MULTIMERIC MOLECULES

(75) Inventor: Dorsey W. Stuart, Mountain View, CA (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/214,699

(22) PCT Filed: Jun. 30, 1997

(86) PCT No.: PCT/US97/11425

§ 371 (c)(1),
(2), (4) Date: Oct. 15, 1999

(87) PCT Pub. No.: WO98/01534

PCT Pub. Date: Jan. 15, 1998

Related U.S. Application Data

(63) Continuation-in-part of application No. 08/678,462, filed on Jul. 9, 1996.

(51) Int. Cl.
*C12Q 1/68* (2006.01)

(52) U.S. Cl. .................. 435/6; 435/254.4; 435/471

(58) Field of Classification Search ............... 435/471, 435/484, 489, 254.4, 6, 7.1, 7.2, 7.21, 254.11
See application file for complete search history.

(56) References Cited

U.S. PATENT DOCUMENTS

| | | | |
|---|---|---|---|
| 4,486,533 | A | 12/1984 | Lambowitz |
| 4,727,037 | A | 2/1988 | Ring |
| 4,816,405 | A | 3/1989 | Yelton et al. |
| 4,880,734 | A | 11/1989 | Burke et al. |
| 4,885,249 | A | 12/1989 | Buxton et al. |
| 4,935,349 | A | 6/1990 | McKnight et al. |
| 5,177,193 | A | 1/1993 | Boime et al. |
| 5,364,770 | A | 11/1994 | Berka et al. |
| 5,643,745 | A | 7/1997 | Stuart |

FOREIGN PATENT DOCUMENTS

| | | |
|---|---|---|
| EP | 552569 | 7/1993 |
| WO | WO-92/06711 | 4/1992 |
| WO | WO95/21263 | 2/1995 |

OTHER PUBLICATIONS

Buczynski, S. et al., *Fungal Genetics Newsletter* (1995 Suppl.) 42A.
Carattoli, A. et al., *Proc. Natl. Acad. Sci. USA* (1995) 92:6612-6616.
Dalbey, R.E. et al., *TIBS* (1992) 17:474-478.
Dales et al., *J. Gen. Microbiol.* (1983) 129:3637-3642.
Downey et al., *Mol. Cell. Biochem.* (1984) 59:155-163.
International Search Report dated Aug. 13, 1997 for corresponding International Application No. PCT/US97/11425.
Kato, E. et al., *Fungal Genetics Newsletter* (1995 Suppl.) 42A.
Koo, K. and Stuart, W.D., *Genome* (1991) 34:644-651.
MacKenzie, D.A. et al., *J. Gen. Microbiol.* (1993) 139:2295-2307.
Nakano, E.T. et al., *Fungal Genetics Newsletter* (1995 Suppl.) 40:54.
Payton et al., *J. Bact.* (1977) 129:1222-1226.
Peberdy, J.F., *Trends in Bio Technology* (1994) 12:50-57.
Perkins et al., "Chromosomal Loci of *Neurospora crassa*", *Microbiological Reviews* (1982) 46:426-570, at 478.
Stuart, W.D. et al., *Genome* (1988) 30:198-203.
Yamashita, R.A. et al., *Fungal Genetics Newsletter* (1995 Suppl.) 42A.
Supplementary European Search Report for 97931506.6, mailed on Feb. 27, 2001, 3 pages.

*Primary Examiner*—James Ketter
(74) *Attorney, Agent, or Firm*—Morrison & Foerster LLP

(57) ABSTRACT

The present invention provides methods and compositions for producing and screening combinatorial libraries of multimeric proteins. The present invention relies on the use of filamentous fungal heterokaryons that are produced using two or more parent strains into which a population of DNA molecules encoding variants of a multimeric protein have been introduced.

15 Claims, No Drawings

METHODS AND COMPOSITIONS FOR COMBINATORIAL-BASED DISCOVERY OF NEW MULTIMERIC MOLECULES

This application is a 371 of PCT/US97/11425, filed Jun. 30, 1997, which is a CIP of U.S. Ser. No. 08/678,462, filed Jul. 9, 1996.

FIELD OF THE INVENTION

The present invention relates to the field of molecular biology and the production of a population of multimeric proteins, particularly heteromultimeric proteins such as antibodies. The present invention specifically provides methods and compositions that provide a population of protein encoding nucleotide sequences in heterokaryonic filamentous fungi that produce a population of multimeric proteins, such as a combinatorial antibody expression library.

BACKGROUND ART

The cloning and expression of heterologous genes in fungi has been used to produce a variety of useful proteins. For example: Lambowitz, U.S. Pat. No. 4,486,533, discloses the autonomous replication of DNA vectors for filamentous fungi by mitochondrial plasmid DNA and the introduction and expression of heterologous genes into *Neurospora*; Yelton et al., U.S. Pat. No. 4,816,405, discloses tools and systems that enable the modification of important strains of filamentous ascomycetes to produce and secrete large quantities of desired heterologous proteins; Buxton et al., U.S. Pat. No. 4,885,249, discloses the transformation of *Aspergillus niger* by a DNA vector that contains a selectable marker capable of being incorporated into the host *A. niger* cells; and McKnight et al., U.S. Pat. No. 4,935,349, discloses a method for expressing higher eukaryotic genes in *Aspergillus* involving promoters capable of directing the expression of a heterologous gene in *Aspergillus* and other filamentous fungi. Similar techniques have been used to clone the mtr gene involved with amino acid transport in *Neurospora crassa* ("*N. crassa*") and to verify the tight linking of the cloned DNA to genomic markers flanking this gene in vivo. Stuart, W. D. et al., *Genome* (1988) 30:198-203; Koo, K. and Stuart, W. D. *Genome* (1991) 34:644-651.

Filamentous fungi possess many characteristics which make them good candidates for use in producing eukaryotic proteins. Filamentous fungi can secrete complex proteins; correctly fold three dimensional proteins including disulfide bond formation; proteolytically clip proteins following translation; and glycosylate proteins using n-linked and o-linked glycosylation reactions. These abilities have made this group of organisms attractive hosts for the production of secreted recombinant proteins. (MacKenzie, D. A. et al., *J Gen Microbiol* (1993) 139:2295-2307; Peberdy, J. F., *Trends in BioTechnology* (1994) 12:50-57).

*Neurospora crassa* has been used as a host cell for recombinant homologous and heterologous protein production. (Carattoli, A., et al., *Proc Nat Acad Sci USA* (1995) 92:6612-6616; Yamashita, R. A. et al., *Fungal Genetics Newsletter* (1995 Suppl.) 42A; Kato, E. et al., *Fungal Genetics Newsletter* (1995 Suppl.) 42A; Buczynski, S. et al. *Fungal Genetics Newsletter* (1995 Suppl.) 42A, Nakano, E. T. et al. *Fungal Genetics Newsletter* (1995 Suppl.) 40:54 ( )). In addition, *Neurospora crassa* has recently been used as a host cell for expressing recombinant heterodimeric and multimeric proteins by means of a heterokaryon., PCT Application WO 95/21263.

A "heterokaryon" (or a heterokaryonic cell) is a cell formed from the fusion of two filamentous fungal parent strains, each heterokaryon cell thus containing two (or more) genetically different nuclei. Heterokaryons contain nuclei from two parent strains that are generally homozygous for all heterokaryon compatibility alleles (except for the mating type allele when the tol gene is present). At least ten chromosomal loci have been identified for heterokaryon incompatibility: het-c, het-d, het-e, het-i, het-5, het-6, het-7, het-8, het-9 and het-10, and more are inferred to exist. Perkins et al, "Chromosomal Loci of *Neurospora crassa*", *Microbiological Reviews* (1982) 46:426-570, at 478.

The present invention advances the work of that disclosed in PCT Application WO 95/21263 by providing methods and compositions for producing a population of multimeric proteins using heterokaryonic filamentous fungi. Such methods and compositions are useful in the discovery and production of panel of multimeric molecules, such as a heterodimeric antibody, multimeric hormones and growth factors and multimeric receptors.

SUMMARY OF THE INVENTION

The present invention provides panels of heterokaryon filamentous fungus that produce variants of multimeric proteins, methods for generating panels of heterokaryon filamentous fungus that produce variants of multimeric proteins, methods of screening panels of heterokaryon filamentous fungus that produce variants of multimeric proteins, and kits containing panels of heterokaryon filamentous fungus that produce variants of multimeric proteins.

The heterokaryon panels of the present invention are generated by fusing a first and second parent fungal strain, each parent strain containing the necessary markers to maintain a heterokaryonic state as well as an expression unit that encodes a naturally occurring variant of a subunit of a multimeric protein, a rationally designed variant of a subunit of a multimeric protein, or a randomly generated variant of a subunit of a multimeric protein. Thus, in addition to natural variants, such as the variable region of an immunoglobulin molecule, variants, generated through the use of chemical, physical or site-directed mutagenesis techniques can be produced.

The heterokaryon panels of the present invention are useful in providing a method of generating heterogeneity in a multimeric protein and then screening the resulting multimeric proteins produced for desired properties. The heterokaryon panels of the present invention are particularly useful in producing and identifying immunoglobulins with desired binding properties such as affinity, avidity and specificity. In addition, a heterokaryon panel can be used to selectively clone previously unidentified multimeric protein subunit encoding nucleic acid molecules.

Based on the above, the present invention provides panels of heterokaryons that produces variants of multimeric proteins, methods of producing a panel of heterokaryons that express variants of multimeric proteins, methods of screening a panel of heterokaryons that produces variants of a multimeric protein, kits that contain a panel of heterokaryons that produces variants of a multimeric protein and methods of using a heterokaryon panel to isolate nucleic acid molecules that encode subunits of a multimeric protein.

DETAILED DESCRIPTION OF THE PREFERRED EMBODIMENTS

The present invention provides novel methods and compositions for generating and screening a population of multimeric proteins. The multimers are generated from an ordered or a random combination of protein subunits. To obtain a panel of multimers, a panel of heterokaryons is obtained in a method comprising the steps of introducing a first and a second population of DNA molecules that encode protein subunits of a multimeric protein into a first and second fungal host parent, forming a panel of heterokaryonic fungal strains using the first and second host fungal parents, and then, if appropriate, culturing the resulting heterokaryon under conditions in which the subunit encoding DNAs are expressed and further screening the resulting panel of heterokaryons for the production of a multimeric protein having the desired properties. Each of the elements, namely the fungal parents, the DNA molecules and the fusion methods are described in detail below. Particularly, when using the present methods for the production of a multivariant library of a multimeric protein, the parent strains used in making the heterokaryon each contain a population of cells, each cell expressing one member of a population of DNA molecules encoding one or more variants of a subunit of the multimeric protein.

Nature of Filamentous Fungi and Background Requirements for Heterokaryon Formation Fungi can occur in single mononucleated cells that yield filamentous multinuclear strands, yeast cells, fruiting bodies with diverse spores, and/or cells that are differentiated sexually. They can also exist in multinucleated forms. The principal element of the growing form of a fungus as a mold is the hypha, a branching tubular structure, about 2 um-10 um in diameter. Hyphae grow by elongation at their tips (apical growth) and by producing side branches. Thus, as a colony grows, its hyphae form a mass of intertwining strands.

Some hyphae penetrate into the culture medium on which the fungus is growing to absorb nutrients, while those hyphae that project above the surface of the medium constitute an "aerial mycelium." Most colonies grow at the surface of liquid or solid media as irregular, dry, filamentous mats. In most species, the hyphae are divided by cross-walls called "septa." These septa, however, have fine, central pores. Thus, even septate hyphae have nuclei that are embedded in a continuous mass of cytoplasm and, in effect, contain a multiplicity of nuclei in a transportable cytoplasm.

The term "filamentous fungi" refers to those fungi that can form a mycelium through a mass of branching, interlocking filaments and, although interrupted by cross walls, permit the passage of cytoplasm between compartments due to perforations in the cross walls. Many of these fungi form meiotic spores within a sac when propagated sexually. With the appropriate stimulation, however, the mechanism of which is not entirely understood, reproduction can occur asexually. In this manner of reproduction, spores known as "conidia" are borne externally at the tips of budding projections formed at various locations along the filaments.

The filamentous fungi used to generate the heterokaryon panels of the present invention are generally Phycomycetes, Ascomycetes, Basidiomycetes, and Deuteromycetes. The Phycomycetes include all non-septate, as well as some septate, filamentous fungi. Their asexual spores are of various kinds and include sporangiospores contained within sacs formed at the end of specialized stalks. Different species have different sexual cycles.

Ascomycetes are distinguished from other fungi by the ascus, a saclike structure containing sexual spores, known as ascospores. The ascospores are the end product of mating, the fusion of male and female nuclei, two meiotic divisions, and usually one final mitotic division. Basidiomycetes are distinguished by sexual spores that form on the surface of a specialized structure. The Deuteromycetes are often referred to as "imperfect fungi" because no sexual phase has yet been observed. Their hyphae are septate, and conidial forms are similar to those of the Ascomycetes.

The preferred filamentous fungus is of the group Ascomycetes, more preferably, from the genera *Neurospora*, *Aspergillus* and *Penicillium*. Particularly useful species from *Neurospora* include *N. intermedia*, *N. crassa*, *N. sitopula*, and *N. tetraspora*, of which the most preferred species is *N. crassa*. Useful species of *Aspergillus* include *A. nidulans*, *A. niger*, *A. terreus*, and *A. fumegatus*.

The vegetative growth of filamentous fungi involves nuclear division with cell division (mitosis). This type of cell division consists of asexual reproduction, i.e., the formation of a new clone without the involvement of gametes and without nuclear fusion by way of conidia. For example, the species of *Neurospora* contain in their nuclei seven different chromosomes, each having a single copy, i.e., the vegetative organism is haploid. This haploid state is typically maintained during mycelial growth and during asexual reproduction through the formation of conidia.

Sexual reproduction can also occur, and then two haploid cells (hyphae or conidia) of different mating type fuse to form a dikaryotic cell containing two distinct nuclei. The two haploid nuclei thus coexist in the same cytoplasm and, for a time, divide more or less in synchrony. If a cell initiates ascospore formation, however, the two different haploid nuclei can actually fuse to form a diploid nucleus, which contains pairs of homologous chromosomes. This diploid cell then begins meiosis.

A "heterokaryon" (or a heterokaryonic cell) is a cell with two (or more) genetically different nuclei. The heterokaryons of the invention must contain nuclei from cells that are homozygous for all heterokaryon compatibility alleles (except for the mating type allele when the tol gene is present). At least ten chromosomal loci have been identified for heterokaryon incompatibility: het-c, het-d, het-e, het-i, het-5, het-6, het-7, het-8, het-9 and het-10, and more are inferred to exist. Perkins et al., "Chromosomal Loci of *Neurospora crassa*", Microbiological Reviews (1982) 46:426-570, at 478.

If two strains carry different alleles at one or more het loci, they are unable to form stable heterokaryons. Protoplasmic killing occurs after fusion of unlike hyphae or after microinjection of cytoplasm or extracts into unlike strains. When duplications (partial diploids) are heterozygous for het one or more alleles, growth is inhibited and highly abnormal. A number of heterokaryon incompatibility loci (specifically, het-c, -d, -e, and -i) were first defined by heterokaryon tests. Het-5 through -10 loci were detected by using duplications, as differences at het loci are common in natural populations. Id.

Mating type alleles "A" and "a" also act as het genes in *N. crassa*, although some slow heterokaryotic growth may occur. Microinjection experiments have implicated proteins in the killing reaction. Thus, opposite mating types are also generally important for the complex events associated with the proliferation of heterokaryotic ascogenous hyphae. Id. at 436 and 478. However, if the tol gene is present, the vegetative (heterokaryon) incompatibility associated with opposite mating type alleles A and a is suppressed without sexual compatibility being affected. Thus, (tol; A+a; a) heterokaryons can be fully compatible and stable if the other het loci are homokaryotic and A/a duplications grow normally when the tol gene is present.

If hyphae from two different strains that are homozygous for the compatibility loci are provided, they may fuse when grown in the same medium, in particular when fusion is forced as described below. The resulting culture will then contain nuclei from both strains circulating in the shared cytoplasm of a common mycelial mat.

The methods and compositions of the present invention provide and use a panel of heterokaryons. As used herein, a "panel of heterokaryons" refers to an array of two or more heterokaryons, where each heterokaryon, or a substantial percentage thereof, produces a different multimeric protein. As described below, the panel of heterokaryons can readily be stored or cultured in a multiwell microtiter plate for efficient screening and propagation.

Construction of Expression Units Encoding a Mixed Population of Protein Subunits In describing the invention, the following terminology will be used in accordance with the definitions set out below:

The invention involves the production of "heterologous multimeric" proteins in the filamentous fungi. In this context, "heterologous" means that the protein is not ordinarily produced by the fungus. "Multimeric" means that the ultimate product is made up of at least two subunits. The multimer may be a heteromultimeric protein, comprised of entirely different subunits, as is the case with immunoglobulins or can be homomultimeric, made up of variants of a single subunit. Examples of multimeric proteins include, but are not limited to, immunoglobulins, prokaryotic or eukaryotic enzymes, blood proteins, hormones, growth factors, toxins and other proteins from pathogens for vaccines, structural proteins, lymphokines, membrane surface proteins, enzyme regulators, transcription regulators, and the like.

Preferred heterodimeric proteins include immunoglobulins, transforming growth factors, antitrypsins, insulin, hemoglobin, multimeric kinases, FSH, LH, hCG, and TSH.

A "nucleotide sequence encoding a protein" is that portion of a sequence for which the transcript is translated into a polypeptide when operably linked to appropriate control sequences. The boundaries of the coding sequence are determined by a start codon at the 5' (amino) terminus and a translation stop codon at the 3' (carboxy) terminus. This coding sequence can be derived from, for example, prokaryotic genes, cDNA from eukaryotic mRNA, genomic DNA sequences from eukaryotic DNA (such as mammalian), or may include synthetic DNA. A polyadenylation signal and transcription termination sequence will usually be located 3' to the coding sequence.

A coding sequence is "operably linked to" control sequences when the control sequences effect the expression of the coding sequence in the appropriate host cell.

An "expression unit" is a DNA molecule that contains a coding sequence operably linked to a "control sequence or region" that directs the transcription and translation of the operably linked sequence in an appropriate host organism under appropriate conditions.

A cell has been "transformed" by exogenous DNA when such exogenous DNA has been introduced into the host cell membrane. For prokaryotes such as bacteria the exogenous DNA may be maintained on an episomal element such as a plasmid. Because filamentous fungi do have nuclei (are eukaryotic), most stably transformed fungus host cells contain the exogenous DNA integrated into a chromosome, so that it is inherited by daughter cells through chromosome replication.

A "recombinant host" refers to cells that have been, are or will be transformed with DNA sequences prepared by recombinant techniques, and includes the cell originally transformed and cultures and progeny thereof.

A variety of methods can be employed to generate a population of DNA molecules that encode 1) naturally occurring variants of a subunit of a multimeric protein, 2) randomly generated or selected variants of a subunit of a multimeric protein, or 3) rationally designed or selected variants of a subunit of a multimeric protein. In the following, an immunoglobulin is used as an illustrative example. A skilled artisan can readily use the methods outlined below, or an equivalent method known in the art, to generate the population of subunit encoding DNA molecules.

A population of DNA molecules that encode naturally occurring variants of a subunit of a protein having natural heterogeneity, such as immunoglobulins, can be produced using standard cDNA generation/cloning techniques. In general, a population of mRNA is first isolated from cells that naturally expresses the multimeric protein, for example, in the case of antibodies, such as from normal or abnormal mammalian spleens. The isolated population of mRNA molecules is then used as a template for the generation of cDNA molecules in art-known cloning methods. For example, the 3' constant region of heavy or light chain genes (or a polyT sequence) can be used to "prime" the generation of a first and second population of cDNA molecules where one population encodes heavy chains and the second population encodes light chains. The populations of cDNA molecules thus produced can be inserted into a suitable expression unit as described below.

Alternatively, site directed or random mutagenesis can be performed on an isolated DNA molecule that encodes a subunit of a multimeric protein to produce non-naturally occurring variants of the particular subunit. Procedures such as random or site-directed mismatched PCR priming, linker-scanning mutagenesis, or chemical and physical mutagenesis can readily be used to generate a population of DNA molecules that encode rationally designed or randomly generated variants of a protein. For example, randomly generated or rationally designed PCR primers can be used to generate random or targeted heterogeneity in a protein encoding sequence, such as the antigen binding site of an immunoglobulin or the active site of an enzyme.

As used herein, a variant is said to be rationally designed when a selection criterion, such as protein folding or selecting a particular target residue or region, is used in generating the variant or selecting the variant-encoding DNA molecules. A variant is said to be randomly generated when a selection criterion is not used when generating or selecting the variant-encoding DNA molecules.

The preferred target site for generating heterogeneity in a multimeric protein subunit is the active site and surrounding amino acid sequences. In the case of the immunoglobulin genes this type of creation of variation would center on the variable regions of each subunit. As an example, one could change each amino acid in the variable region one by one to produce a library of known variation.

Construction of Expression Units Encoding Subunits of the Multimeric Protein

The expression units containing a nucleotide molecule encoding a subunit of a multimeric protein are constructed using well known techniques. In general, an expression unit is generated by placing the subunit coding sequences into operable linkage with control sequences that directs the expression of the subunit encoding sequences in the ultimate filamentous fungus host.

A variety of control elements are presently known in the art for directing the expression of an operably linked protein encoding sequence in either a constitutive or inducible fashion. The choice of a control sequence will be based on the fungal strain used, conditions employed for culturing the fungus, the level of protein expression desired, and the nature of expression required (for example, inducible versus constitutive). A skilled artisan can readily utilize art-known control sequences for generating the expression units used in the present heterokaryon panel.

In addition to sequences that direct the transcription and translation of the protein-encoding sequence, the expression units of the present invention may further control signal sequences, expression control elements that direct the export of a protein outside the cell. A review of secretory signals that are known in filamentous fungus are provided by Dalbey R. E., et al., *TIBS* 17:474-478 (1992). The skilled artisan can readily generate expression units that contain secretory signals.

In one application, recombination units are generated instead of the expression units. In such a use, the subunit encoding sequence, or fragment of a subunit encoding sequence, is flanked by regions of DNA that contain sequences that are homologous to an integration site in the host fungal strain. The homologous sequences are then used to stimulate and direct homologous recombination between the recombination units and the host chromosome. When recombination units are used, the host strain is preferably first transformed with an expression unit that contains an expression control element followed by sequences that are used for targeted recombination. For example an immunoglobulin heavy or light chain can be introduced into a host fungus and then homologous recombination units can be used to introduce heterogeneity within a targeted region of the host chromosome.

Intermediate hosts are sometimes used to produce intermediate vectors capable of transforming the ultimate fungal cells. The intermediate bacterial transformants can then be grown to obtain the desired quantities of DNA, which can be used to transform a desired filamentous fungus host. Examples of commonly available bacterial vectors that can serve as intermediate vectors include, for example, pBR322, pUC8 and pUC9. Additional useful intermediate vectors include pHY201, pKBY2, pTZ18R, pX182 and pCVN2.9, pN807, pN846.

It will be understood that this description and disclosure of the invention is intended to cover all embodiments that are within the spirit and scope of the invention. For example, it is within the knowledge of the art to insert, delete or substitute amino acids within the amino acid sequence of an open reading frame without substantially affecting the activity of the molecule, and such multimeric subunits can be generated with deletions, additions or substitutions to the naturally occurring subunit are included in the invention.

Nature of the Parent Strains

Since each of the parent fungal strains used in making the panel of heterokaryons of the present invention will contain a member of a population of DNA molecules that encodes a subunit of a multimeric protein, one fungal parent will have a nucleus modified to contain a member of a first population of DNA molecules that encodes a first subunit of a desired multimeric protein and the second fungal parent will have a nucleus modified to contain a member of a second population of DNA molecules that encodes a second subunit of a desired multimeric protein. If the multimeric protein is comprised of two or more copies of a single subunit, the first and second population of DNA molecules can be the same. If the multimeric protein is comprised of two or more different subunits, the first and second populations of DNA molecules will encode different subunits. For example, to produce a panel of heterokaryon producing antibody molecules, one fungal parent will produce an immunoglobulin light chain while the other fungal parent will produce an immunoglobulin heavy chain.

In addition to having been modified to contain a DNA molecule encoding the protein subunit, as described above, the nuclei of each of the parent strains must contain a genome that results in a characteristic that renders the fungus dependent on the presence of the second nucleus for survival and under the conditions used to form the heterokaryon. Thus, the nucleus of each parent confers a characteristic which would result in the failure of the fungus in which it is contained to survive under the culture conditions unless the second nucleus is also present. For example, a parent that requires a particular nutrient may be cultured on a medium lacking the nutrient along with a parent that does not have this requirement. If hyphal fusion occurs, the nucleus of the second parent confers ability to survive in the absence of this nutrient. The second parent, in turn, may require a different nutrient, not required by the first. Only fungi containing both nuclei can then survive when both nutrients are lacking.

The required nutrient can be any substance which the fungus strain cell needs for growth or which, when absent, seriously impairs the ability of the fungus strain to grow or survive. Examples of useful nutrient requirements and the relevant mutants include:

(1) amino acids such as histidine (his-1 through -7 mutants), proline (aga mutants), arginine (arg-11 mutants), citrulline (arg-11 mutants), asparagine (asn mutants), choline (chol-1 and chol-2 mutants), cysteine (cys-1 mutants), glutamine (gln-1 mutants), leucine (leu-1 through -4), lysine (lys-2, -4 and -5), methionine (mac mutants and met-6, -9 and -10 mutants), and threonine (thr-2 and -3 mutants);

(2) mixtures of aromatic amino acids, such as a mixture of p-aminobenzoic acid, tyrosine, tryptophan, and phenylalanine (required by all aro strains except aro-6, aro-7 and aro-8), a mixture of tryptophan and phenylalanine (required for aro-6 mutants), a mixture of isoleucine and valine (required for ilv-1, -2 and -3), and a mixture of phenylalanine and tyrosine (required for pt mutants);

(3) vitamins such as pantothenic acid (pan-1 mutants) and thiamine (thi-2 and thi-4 mutants);

(4) purine bases such as adenine (ad-2 through ad-4 and ad-8 mutants), hypoxanthine (ad-2 and ad-3 mutants), inosine, and guanine or guanosine (gua-1 or -2 mutants);

(5) pyrimidine bases such as uracil (pyr-1 through pyr-6);

(6) saturated fatty acids (cel mutants) or unsaturated fatty acids such as $C_{16}$ or $C_{18}$ fatty acids having a double bond in the cis conformation at either the 9- or 11-position, fatty acids with a double bond in the trans configuration at the 9-position, and fatty acids with multiple cis double bonds interrupted by methylene bridges (ufa-1 and -2);

(7) physiologically important ions such as potassium (trk);

(8) sugar alcohols such as inositol (acu mutants and inl mutants) and glycerol; and (9) other organic entities such as acetate (ace mutants), I-ketoglutarate, succinate, malate, formate or formaldehyde (for mutants), p-aminobenzoic acid (pab-1, -2 and -3 mutants), and sulfonamide (sfo mutants at 35° C.).

One specific example based on a nutritional requirement is the Arg B+ gene coding for the enzyme ornithine transcarbamylase. This enzyme is present in wild type *A. niger*. Mutants lacking this enzyme (Arg B− strains) can be prepared by usual non-specific techniques, such as treatment with ultraviolet radiation, followed by screening based on an inability to grow on minimal medium, coupled with an ability to grow on a medium containing arginine. Fungi containing this genome will grow on minimal medium if they also include an ArgB+ nucleus.

Also useful for forcing heterokaryon formation are genes conferring a resistance to any one of a variety of cytotoxic agents. For example, in an alternative embodiment, one of the parents can have a requirement for a nutrient as well as a resistance to a toxic effect induced by a noxious chemical, an antibiotic or virus, or a harsh environmental conditions such as a predetermined temperature range to which the other parent is sensitive.

Specific examples of noxious chemicals that can exert a toxic effect include acriflavine (resistance conferred by acr generally, with the presence of the shg gene being required for resistance by acr-4 and acr-6); 3-amino-1,2,4-triazole (resistance conferred by acr-2, atr-1, cpc, leu-1 or leu-2)); dyes such as malachite green (resistance conferred by acr-3); caffeine (resistance conferred by caf-1); purine analogs (resistance to 8-azaadenine and 2,6-diaminopurine conferred by aza-1; resistance to 8-azaadenine and 8-azaguanine conferred by aza-2; resistance to 8-azaguanine and 6-mercaptopurine conferred by aza-3; resistance to 6-methylpurine conferred by mep(3) and mep(10); cyanide (insensitivity conferred by cni-1 in the first 24 hours of growth); tetrazolium (resistance conferred by cya-6 and cya-7); cycloheximide (resistance conferred by cyh-1, -2 and -3); chromate (resistance conferred by cys-13); 2-deoxy-D-glucose (resistance conferred by dgr$^-$); edeine (resistance conferred by edr-1 and -2); ethionine (resistance conferred by eth-1, by nap in the presence of p-fluorophenylalanine, and by oxD if the ethionine is in the D form); fluoro compounds such as 5-fluorodeoxyuridine, 5-fluorouracil, and 5-fluorouridine (resistance to all three conferred by fdu-2; resistance to 5-fluorouracil being conferred by uc-5 in an ammonia-free minimal medium; resistance to 5-fluorodeoxyuridine and 5-fluorouridine being conferred by ud-1), and fluorophenylalanine (resistance conferred by fpr-1 through -6 under certain conditions); 8-azaadenine (resistance conferred by mts); methyl methane sulfonate (insensitive or marginally sensitive for upr-1); surface-active agents such as dequalinium chloride, cetyltrimethyl ammonium bromide, and benzalkonium chloride (resistance conferred by sur-1); and metal ions such as vanadate (resistance conferred by van).

Examples of antibiotics typically exerting a toxic effect include benomyl [methyl-1-(butylcarbamolbenzimidazol-2-yl carbamate] (resistance conferred by Bml); antimycin A (insensitivity conferred by cni-1 in the first 24 hours of growth); polyene antibiotics such as nystatin (resistance conferred by erg-1 and -3); and oligomycin (resistance conferred by oli).

Also useful are genes conferring resistance to extremes in various environmental conditions such as a high or low temperature, the lack of oxygen (resistance conferred by an), constant light (resistance conferred by lis-1, -2 and -3) or the absence of light, UV radiation, ionizing radiation, and high or low osmotic pressures. In a particularly preferred embodiment, the resistance to a toxic effect is a resistance to an antibiotic such as ampicillin.

Strains generally useful in the invention can be grown on 1× Vogel's Minimal Medium (N medium) in cotton-plugged test tubes, with supplements being added depending on the phenotype of the strain, such as, for example, histidine, arginine and/or inositol. Typical strains may be obtained, for example, from the Fungal Genetics Stock Center ("FGSC") and from D. D. Perkins, Stanford University. Another *N. crassa* strain believed to be useful is M246-89601-2A (obtained from Dr. Mary Case, University of Georgia, Athens). This strain is a derivative of wild-type 74A, which contains a stable qa-2 mutation (M246), an arom-9 mutation (M6-11), and an inos (io601) mutation. The double mutant qa-2, arom-9, lacks both the biosynthetic and catabolic dehydroquinase activities and is unable to grow on minimal medium without a supplement of aromatic amino acids, such as, for example, phenylalanine at a concentration of about 80 µg per ml.

Useful strains of *A. niger* (ATCC 46951) are also available from the Fungal Gentics Stock Center, as well as strains of *Fusarium, Gelasinospora*, and *Sordaria fimicola*, or can be prepared by mutagenizing with UV light to form an isolate that requires ornithine or arginine for growth in a defined minimal media. This strain, which lacks ornithine carbamoyl transferase, has been called arg B (350(–)52). Media for growing *A. niger* or *A. nidulans* are described by Cove, *Biochim Biophys Acta* (1966) 113:51-56.

Standard procedures are generally used for the maintenance of strains and the preparation of conidia (Davis and de Serres, *Methods Enzymol* (1971) 17A:79-141). Mycelia are typically grown in liquid cultures for about 14 hours (25° C.), as described in Lambowitz et al. *J Cell Biol* (1979) 82:17-31. Host strains can generally be grown in either Vogel's or Fries minimal medium supplemented with the appropriate nutrient(s), such as, for example, histidine; arginine; phe, tyr, and/or trp (each about 80 µg per ml); p-aminobenzoic acid (about 2 µg per ml); and inositol (about 0.2 mg per ml).

Many fungal strains with the desired characteristics are publicly available. If not readily available, however, one of ordinary skill in the art can use selection techniques well-known in the art for separating out either the desired mutants or the engineered nuclei providing the desired characteristic. Illustrative parental combinations are shown in the table below.

TABLE 2

| First Nucleus | | Second Nucleus | | |
|---|---|---|---|---|
| First Characteristic | Second Property | Second Characteristic | First Property | Fusion Conditions |
| his- | arg$^+$ | arg$^-$ | his$^+$ | minimal medium (mM) |
| his- cyclohex$^s$ | bm$^r$ bm$^r$ | bm$^s$ bm$^s$ | his$^+$ cyclohex$^r$ | MM + bm MM + bm + cyclohex |
| caffeine$^s$ | arg$^+$ | arg$^-$ | caf-1 | MM + caffeine |
| Thi-2 | wt | aro-6 | wt | MM + thiamine + trp + phe |

As seen in the table, a variety of complementary characteristic/property combinations can be chosen to fit various fusion conditions. In general, the nutrient requirement is manifested by a mutant strain, while the ability to resist certain substances may more conveniently be conferred by modification of the nucleus with an expression system for the resistance gene. Alternatively, the nutritional requirement can be effected using recombinant techniques such as homologous recombination with a transforming vector and the resistance can be conferred by mutation under conditions where the toxic conditions are present.

In one embodiment of the invention, host cells are converted to spheroplasts for transformation. When spheroplasts are used, a preferred method or preparing them is by enzymatic digestion of the cell walls, for example, by using a chitinase/glutamase mixture. The selection of a suitable enzyme for enzymatic digestion is within the skill of the art. Useful enzymes are those capable of digesting complex polysaccharides, and are found among those known as effective in preparing fungal spheroplasts of a wide variety of fungal species. Specific examples of suitable enzymes include Novozym 234 (an impure mixture of enzymes) and J-glucuronidase. Other suitable methods may be used to form spheroplasts. If suitable methods for cell wall penetration by the use of vectors are identified, however, whole cells of the fungal host may be used along with or instead of spheroplasts.

To modify the nucleus of the first fungus host strain to contain an expression unit for a DNA encoding a particular subunit of multimeric protein, the practice of the invention employs, unless otherwise indicated, molecular biology, microbiology, and recombinant DNA techniques that is within the skill of the art. Such techniques are explained fully in the literature. See, e.g., Maniatis et al., *Molecular Cloning: A Laboratory Manual* (1982); D. N. Gover et al *DNA Cloning: A Practical Approach* (1985) Volumes I and II; *Oligonucleotide Synthesis* (M. J. Gait ed. 1984); *Nuclei Acid Hybridization* (Hames et al. eds. 1985); *Transcription and Translation* (Hames et al. eds. 1984); *Animal Cell Culture* (R. I. Freshney ed. 1986); *Immobilized Cells and Enzymes* (IRL Press 1986); B. Perbal, *A Practical Guide to Molecular Cloning* (1984).

General Procedure for Transformation of *N. crassa*

Once the population of DNA molecules encoding the multimeric subunits is placed into expression units, the DNA molecules are used to transform parent host strains of a filamentous fungus, such as described by Stuart, "Heterologous dimeric proteins produced in heterokaryons." Strains of *Neurospora crassa*, are publicly available from the Fungal Genetics Stock Center, but independently prepares strains can also be used. Mutants may be isolated de novo, as illustrated by Stadler et al. *Genetics* (1966) 54:677-685 and Haas et al. *Genetics* (1952) 37:217-26. Useful strains can also be obtained from D. D. Perkins from Stanford University. Strains are typically grown on 1× Vogel's Minimal Medium ("N medium") in cotton-plugged test tubes, with appropriate supplements being added depending on the strain's phenotype.

Spheroplasts are used as subjects for transformation. To form conidial spheroplasts, the fungus is inoculated onto 25 ml of solid N medium, with appropriate supplements in four to five 125-ml Erlenmeyer flasks, which have been plugged with cotton. The cultures are grown at room temperature for 5-7 days.

The conidia are harvested by adding 10 ml of N medium to each flask, replacing the cotton plug, and swirling the flask. The solids are allowed to settle for a few minutes. The conidial mixture is poured to an autoclaved cheesecloth bag hanging in the mouth of an Erlenmeyer flask and secured with one or more rubber bands. The filtrate is recovered, and the concentration of conidia is determined by a hemocytometer count, with chains being counted as one.

A volume of $2\times10^9$ conidia is added to 150 ml of liquid N medium containing 1.5% sucrose and appropriate supplements. The conidia are germinated in the cotton-plugged flask while shaking (150-200 rpm) for 5-6 hours at room temperature until more than 75% have germinated and the germ tubes are 1-4 conidial diameters in length. The cells are harvested by centrifuging at about 1500-2000 rpm for 10 minutes. The cell pellet is rinsed three times with water.

The pellet is then re-suspended in 10 ml of 1.0 M sorbitol, and the spheroplasts are prepared by enzymatic removal of the tough conidial cell wall with an enzyme under isotonic conditions, to prevent the "bursting" of the spheroplasts as they are formed. The protocol is adapted from the method of Vollmer and Yanofsky, *Proc Natl Acad Sci USA* (1986) 83:4869-73.

Specifically, in a sterile 250 ml Erlenmeyer flask, the conidial suspension is generally added to 50 mg of a solid enzyme sold by Novo Laboratories under the trade name Novozym 234. The mixture is shaken (100 rpm) at 30° C. for about an hour (±10 minutes) to digest the cell wall. The spheroplast formation process is monitored by examining a small aliquot of the mixture microscopically under a cover slip. Spheroplasts can be detected because they lyse osmotically when water is applied to one end of the cover slip. The process should be monitored frequently at the later stages of spheroplast formation.

The spheroplast mixture is decanted into a sterile 15-ml conical centrifuge tube, and the spheroplasts are recovered by centrifuging at 500 rpm (10 minutes) in a swinging bucket table top centrifuge. The resulting pellet is rinsed twice with 10 of 1.0 M sorbitol and then once with the following STC solution: 91 g sorbitol; 50 mM Tris. Cl; 50 mM $CaCl_2$; sufficient NaOH to adjust the pH to 8.0; and q.s. to 500 ml.

The final spheroplast pellet is suspended in a mixture of 16.0 ml STC, 200 UIDMSO, and 4 ml of the following PTC solution: 200 g polyethylene glycol sold under the trade name "4000" by Sigma; 50 mM Tris. Cl; 50 mM $CaCl_2$; sufficient NaOH to adjust the pH to 8.0; and q.s. to 50 ml.

The resulting suspension of spheroplasts can either be used directly or stored frozen in 1.0 ml aliquots at −80° C.

In a sterile, 15-ml screw-cap tube, 2.0 ul of 50 mM Spermidine solution, 5.0 ul of the plasmid DNA to be transfected, such as that containing the expression system for a subunit of the desired heterodimer along with a selectable marker such as benomyl resistance (usually at a concentration of about 1.0 mg/ml) and 5.0 ul of a 5 mg/ml heparin solution are mixed by flicking the tube. The spermidine solution is prepared by dissolving 12.73 mg of spermidine in 1.0 ml TE and adjusting the pH to 8.0, and can be stored at −20° C. The heparin solution is prepared by dissolving 50 mg of the sodium salt of heparin in 10 ml of STC and can be stored in frozen aliquots.

The contents of the tube are briefly spun (pulsed) in a tabletop centrifuge and then placed in an ice bath. About 50-100 ul of thawed spheroplasts are added to the tube. The mixture is then incubated on ice about 30 minutes, but incubation periods of about 20 minutes on ice have been successful. About 1 ml of PTC is added and mixed well by flicking the tube. The mixture is incubated further at room temperature for about 20 minutes.

A Regeneration "Top" Agar is prepared by mixing: 20 ml 50×Vogel's Minimal Medium; 825 ml of water; 182 g sorbitol; and 28 g agar. The top agar is autoclaved and 100 ml of a 10× FIGS solution (containing 5 g/l fructose, 2 g/l inositol, 2 g/l glucose, and 200 sorbose) is added. 15 ml of the top agar is incubated at 50-55° C. and poured into the tube containing the spheroplasts and plasmid DNA. The contents are quickly mixed by flicking and inverting the tube 2-3 times and then uniformly poured onto a layer of plating "bottom" agar.

The "bottom" agar is prepared by mixing any required supplements, in 1× N medium; autoclaving; and adding 10× FIGS and benomyl (if benomyl resistance is used as a marker) to final concentrations of 1× and 0.5 µg/ml respectively. A volume of 25 ml of "bottom" agar is poured into a petri plate and allowed to harden.

After the top agar has been poured over the bottom agar, bubbles are removed by flaming. The plates are kept in an upright position until the top agar has solidified (about 5 minutes). If the top agar tends to harden prematurely, the bottom agar plates can be prewarmed. Once the top agar has solidified, the plates are incubated in an inverted position at 30° C.

For selection of the *N. crassa* transformants, the host is thus cultured on the appropriate medium (having composition only the transformed cells can utilize or containing an antibiotic to which only transformed cells are resistant) and incubated at about 34° C. An indication of a successful transformation can be seen about 24-36 hours after plating. Stable transformants are generally scored after three days of growth. The incubation period to detect transformants will vary depending on the host strain and the phenotypic marker.

Selected transformants can be screened for, expression of the desired protein subunit by standard methods, such as an appropriate ELISA, a colony blot immunoassay, restriction enzyme analysis, filter hybridization, nested deletion subcloning, and the like.

In the present invention, the above-described recombinant techniques are used to produce:

(1) a first fungus having a first characteristic that negatively affects growth under specified conditions but is correctable by a property conferred by a second nucleus; the first fungus now transformed to contain an expression unit for a nucleotide sequence encoding a first subunit; and (2) a second fungus having a second characteristic that negatively affects growth under specified conditions but is correctable by a property conferred by the first nucleus; the second fungus now contains an expression unit for a nucleotide sequence encoding the second subunit The resulting first and second strains are the parents used to form the heterokaryons of the invention.

Alternatively, electroporation procedures can be used to transform freshly harvested conidia of filamentous fungus such as *Neurospora crassa* (Van, D. C. *Fungal Genetics Newsletter No. 42A* (Supplement) (1995)). In general, conidia are harvested from 7-28 day old cultures. The cells are washed in 1 M sorbitol solution and suspended at a final concentration of $2.5 \times 10^9$ cells/ml. Approximately 5 ug of linearized DNA is added to an aliquot of the conidial suspension and a portion of this is placed in the bottom of an electroporation cuvette, for example an electroporation cuvette with a 0.2 cm gap. An electroporator, such as an InVitrogen Electroporator II, is set with a voltage gradient of about 7.25 kb/cm and a setting of about 71 uF and about 200 ohms. Following electroporation, the cells are plated on appropriate media with or without a top agar essentially as described above.

Following transformation, a stable production strain derived form each molecular variant is established by expanding the culture on selective media for the particular host cell and expression unit used in each individual case.

Production of the Heterokaryon

Because the first fungus strain and the second fungus strain are chosen to be homozygous with respect to all heterokaryon compatibility alleles (with the exception of the mating allele when the tol gene is present as explained above), when the first and second fungus are cultured together under conditions wherein neither the first fungus nor the second fungus can survive alone the fungi are fused so that the heterokaryotic fungus of the invention is formed. By hyphal fusion, the different haploid nuclei of the first and second fungi come to coexist in a common cytoplasm. While not wishing to be bound by any theory, applicants believe membrane fusion results from the aggregation of intramembranous particles within each cell, making possible cell contacts between protein-free areas. Rearrangement of the lipids in the contact areas then leads to full fusion.

Because each of the two parents contains a nucleus which produces different subunits of the multimeric protein, the resulting heterokaryon is capable of producing the completed multimeric protein comprising both subunits.

The heterokaryon thus generated is stable, with the two nuclei dividing at about the same rate. When heterokaryons having two (or more) nuclei are formed, it is also possible to form some mononucleated hybrid cells if the nuclei enter mitosis at approximately the same time as they fuse. This type of nuclear fusion does yield heterozygous diploid nuclei when it occurs, but it is rare, and the diploid nuclei formed are usually greatly outnumbered by the haploid nuclei.

Panel of Heterokaryons

The compositions and methods of the present invention employ a panel of heterokaryons. As described above, the panel comprises two or more heterokaryons, each heterokaryon producing a different multimeric protein. The preferred panels of the present invention will contain more than two members, the more preferred containing more than ten members, the most preferred containing more than twenty members. One example of the panel of heterokaryons is a panel that produces immunoglobulin variants. For example, to generate such a panel, conidial suspensions of each individual strain are mixed in a matrix using a microtiter plate or other convenient format such as illustrated in the following matrix:

| VARIANT | Kappa 1 | Kappa 2 | Kappa 3 | Kappa 4 |
|---|---|---|---|---|
| Gamma 1 | k1g1 | k2g1 | k3g1 | k4g1 |
| Gamma 2 | k1g2 | k2g2 | k3g2 | k4g2 |
| Gamma 3 | k1g3 | k2g3 | k3g3 | k4g3 |
| Gamma 4 | k1g4 | k2g4 | k3g4 | k4g4 |
| Gamma 5 | k1g5 | k2g5 | k3g5 | k4g5 |

In this illustration, 20 unique combinations are produced. In a standard microtiter plate culture dish, 96 unique combinations would be produced if 12 variants of one subunit were arrayed against 8 variants of the second subunit.

Alternatively, the panel can comprise a random mix of parental strains as opposed to the characterized strains illustrated above. In such an arrangement, the panel will comprise two or more heterokaryons in a random array. Further, an antibody producing heterokaryon panel can be generated by fusing a first population, or individual members of a first population, of a parent fungal strain that express a heavy immunoglobulin chain with a second population, or individual members of a second population, of a parent fungal strain that express a light immunoglobulin chain. After fusing, the resulting heterokaryons are arrayed to form a panel of heterokaryons that produces antibody molecules.

As described previously, the microtiter plate contains minimal medium (without agar if in liquid form) which will not support the growth of any parent strain alone but which will support the growth of a heterokaryon culture composed of nuclei from one of each of the two parent strains. For example, if each of the fusing fungal strains carry an auxotrophic requirement different from the other, the only cells capable of growing in culture media where both of the nutrients are absent will be complementary heterokaryons which are also capable of expressing the subunits of the multimeric protein. For example, one strain may require an amino acid, such as arginine, while the other strain may require a base, such as adenine. Each strain can be independently maintained on media supplemented with the appropriate extra metabolite, but neither strain can survive alone on minimal media. The heterokaryons, however, will survive on minimal media because each nucleus complements the other's requirement.

A typical minimal medium contains: per liter, 5.0 g Dextrose, 50.0 mls of a Salt Solution (below), 1.0 ml trace elements (below), and 12.5 g Agar (adjusted pH 6.5) if the media is to be in solid form. The Salt Solution contains: 120.0 g $NaNO_3$, 10.4 g KCl, 10.4 g $MgSO_4$, and 30.4 g $KH_2PO_4$.

The trace element solution contains: 1.1 g $(NH_4)_6Mo_7O_{24}.4H_2O$, 11.0 g $H_3BO_3$, 1.6 g $CoCl_2.6H_2O$, 1.6 g $CuSO_4$, 50.0 g $Na_2EDTA$, 5.0 g $FeSO_4.7H_2O$, 5.0 g $MnCl_2.4H_2O$, and 22.0 g $ZnSO_4.7H_2O$ (pH 6.5).

Thus, to maintain the heterokaryotic filamentous fungus in its heterokaryotic state, external forcing is maintained. Growing the heterokaryotic fungal cells on minimal media "forces" the strains to remain together. If mating types are opposite, the presence of the tol gene can be used to maintain stable (A+a) heterokaryons.

The multimeric protein is produced by culturing the panel heterokaryons of the invention under conditions favorable to production of the protein. The multimer may be recovered from the culture and purified in accordance with standard techniques adapted, of course, as necessary to preserve the structure of the multimer.

Preferably, the heterokaryotic filamentous fungus carries an expression unit that allows the host being cultured to secrete the desired multimeric protein directly into a minimal growth medium, so that the multimeric protein(s) can be purified directly from cell-free medium. Intracellularly produced multimeric protein can be isolated from cell lysates. Useful purification methods in accordance with known procedures are within the skill of the art, such as, for example, molecular size exclusion, ion-exchange chromatography, HPLC, affinity chromatography, hydrophobic interaction chromatography, and the like.

Assay for Secreted Proteins

Microtiter plates are commercially available which are sterile, contain filters of known sizes in the bottom of each well (e.g. 0.6 micron or 0.45 micron pore sizes) and which, when placed on a commercially available vacuum filter holder will deposit liquid media through the filter, into a second identically configured microtiter plate, keeping the media in the same order as the cells and the culture plate all the while maintaining the sterility of the original heterokaryon culture in the original culture plate.

The collected media can be tested for the desirable improved characteristic, increased or decreased activity, binding, toxicity or any other characteristic which can be measured. During this testing activity, the original fungal heterokaryotic cell cultures can be stores at 4° C. or, if the testing is expected to require more than a week, the culture plate can be stored frozen with or without a cryopreservative added.

Upon identification of a culture that is producing a desirable variant of the multimeric molecule, the cells can be removed from the culture plate and cultured on solid medium and after sufficient growth used to inoculate an expanded liquid culture. Alternately, the original strains used to inoculated the matrix constructed in the microtiter format can be mixed directed together as used for an expanded culture. When grown under whatever the optimal conditions are for the particular fungal host used, this expanded host culture will produce the desired product is sufficient quantities for further research evaluation.

Assay for Non-Secreted Proteins

If the protein is not secreted, the cell mass in each microtiter plate can be removed, disrupted by standard methods and the cell supernatant and debris assayed for the multimeric protein with desirable characteristics. Once the strain combination that produces the desired variant has been identified, the original strains used to inoculate the matrix constructed in the microtiter format can be mixed together and used to make an expanded culture. Again, when grown under optimal conditions for the particular heterokaryon, this expanded host culture will produce the desired product in sufficient quantities for further evaluation and use.

Other Uses for a Heterokaryon Panel

The heterokaryon panel of the present invention can also be used to isolate a subunit encoding DNA molecule of a multimeric protein when one or more of the other subunits of the multimeric protein has been isolated. In such a use, the first population of DNA molecules will comprise the nucleotide sequence that encodes the known subunit. The second population of DNA molecules will be randomly or rationally selected cDNA or genomic clones isolated from the organism that naturally produces the multimeric protein in question. As described above, the heterokaryon panel is formed by fusing members of a first and a second population of parent fungal strains, each containing a member of their respective population of expression units. The member of the heterokaryon panel that expresses the reconstituted multimeric proteins can readily be detected based on the production of the reconstituted multimeric protein.

Kit Containing Heterokaryon Panels

The present invention further provides kits containing one or more containers that contain a heterokaryon panel of the present invention. As used herein, a container refers to a physical device into which cells can be placed and stored. The preferred container contains an array into which the panel can be placed for culturing or storage. One example of such a container is a 96 well microtiter plates. A skilled artisan can readily adapt any of the available container means so that it holds a heterokaryon panel of the present invention.

The following examples are intended to illustrate but not to limit the invention.

The invention claimed is:

1. A panel comprising two or more heterokaryons wherein each of said heterokaryons produces a different variant of a multimeric protein and each heterokaryon is formed by fusing a first and a second fungal parent strain, wherein said heterokaryon requires the presence of both fungal parent nuclei for survival, said first and said second parent fungal strain each contain an exogenously supplied nucleic acid molecule that encodes a variant of a subunit of a multimeric protein, wherein at least one exogenously supplied nucleic acid molecule is randomly generated or rationally designed, and where said first and said second parent strains are homozygous for all heterokaryon compatibility alleles.

2. The panel of claim 1 wherein at least one variant of a subunit of a multimeric protein is naturally occurring.

3. The panel of claim 1 wherein said multimeric protein is a heteromultimeric protein.

4. The panel of claim 1 wherein each of said multimeric proteins is an antibody molecule.

5. The panel of claim 1 wherein each of said multimeric protein is secreted into the medium.

6. A kit comprising one or more containers that contains the heterokaryon panel of claim 1.

7. A method for producing a panel of heterokaryons comprising two or more heterokaryons wherein each of said heterokaryons produces a multimeric protein comprising the steps of:
    fusing at least a pair of first and second fungal parent strains, said first and said second parent fungal strains each containing an exogenously supplied nucleic acid molecule that encodes a variant of a subunit of a multimeric protein, wherein at least one exogenously supplied nucleic acid molecule is randomly generated or rationally designed, and where said first and said second parent strains are homozygous for all heterokaryon compatibility alleles and
    selecting two or more heterokaryons thus formed to generate said panel,
    wherein said heterokaryon requires the presence of both fungal parent nuclei for survival.

8. The method of claim 7 wherein at least one variant of a subunit of a multimeric protein is naturally occurring.

9. The method of claim 7 wherein said multimeric protein is a heteromultimeric protein.

10. The method of claim 7 wherein said multimeric protein is an antibody molecule.

11. The method of claim 7 wherein said multimeric protein is secreted into the media under appropriate conditions.

12. The method of claim 7 wherein said first and second parent fungal strains is fused using a pulsed electric field.

13. A method to produce a panel of variants of a multimeric protein, said method comprising the step of culturing the heterokaryon panel of claim 1 under conditions in which the exogenously supplied nucleic acid molecules are expressed so as to form variants of a multimeric protein.

14. A method to identify an agent that binds to a member of a panel of variants of a multimeric protein, said method comprising the step of incubating a panel
    comprising two or more heterokaryons wherein each of said heterokaryons produces a different variant of a multimeric protein and each heterokaryon is formed by fusing a first and a second fungal parent strain, wherein said heterokaryon requires the presence of both fungal parent nuclei for survival, said first and said second parent fungal strain each contain an exogenously supplied nucleic acid molecule that encodes a variant of a subunit of a multimeric protein and where said first and said second parent strains are homozygous for all heterokaryon compatibility alleles
    with an agent to be tested and determining whether said agent binds to one or more heterokaryons of said panel.

15. A method to identify an agent that binds to a member of a panel of variants of a multimeric protein, said method comprising the steps of incubating the panel of any one of claims 1-5 with an agent to be tested and determining whether said agent binds to one or more heterokaryons of said panel.

* * * * *